United States Patent [19]

Marguerie de Rotrou

[11] Patent Number: 5,100,875

[45] Date of Patent: Mar. 31, 1992

[54] NOVEL PEPTIDES HAVING PLATELER AGGREGATION INHIBITORY ACTIVITY

[75] Inventor: Gerard A. Marguerie de Rotrou, Grenoble, France

[73] Assignees: Institut National de la Sante et de la Recherche Medicale (INSERM), Paris; Laboratoire L. Lafon, both of France

[21] Appl. No.: 600,123

[22] Filed: Oct. 22, 1990

Related U.S. Application Data

[63] Continuation of Ser. No. 130,863, Dec. 10, 1987, abandoned.

[30] Foreign Application Priority Data

Dec. 15, 1986 [FR] France .................... 8617507
Jun. 25, 1987 [FR] France .................... 8708986

[51] Int. Cl.$^5$ .................... A61K 37/02; C07K 5/10
[52] U.S. Cl. .................... 514/18; 530/330
[58] Field of Search .................... 514/18; 530/330

[56] References Cited

U.S. PATENT DOCUMENTS 4,683,291  7/1987  Zimmerman et al. .............. 530/330
4,792,525  12/1988 Ruoslahti et al. .................. 530/330
4,857,508  8/1989  Adams et al. ...................... 514/18

FOREIGN PATENT DOCUMENTS 0164654  12/1985  European Pat. Off. .
0220957  5/1987   European Pat. Off. .
2608160  12/1986  France .

OTHER PUBLICATIONS

Boucaut, J. C., et al., "Biological Active Synthetic Peptides as Probes of Embryonic Development: A Competitive Peptide Inhibitor of . . . ", Chemical Abstracts, vol. 102, p. 428, No. 21570a (1985).

Chen, W. T., et al., "Regulation of Fibronectin Receptor Distribution by Transformation, Exogenous Fibronectin, and Synthetic Peptides", Chemical Abstracts, vol. 106, p. 353, 1987.

Ruoslahti, R. et al., *Falk Symposium*, 43 (Modulation Liver Cell Expression), pp. 239–244, 1987.

Alberts, B. et al., *Molecular Biology of the Cell*, Garland Publishing, Inc., pp. 59, 1983.

Pierschbacher, M. et al., *Journal of Biological Chemistry*, 262(36): 17294–17298, 1987.

Dayoff, M., Atlas of Protein Sequence and Structure, vol. 5: 89–99, 1972.

*Proc. Natl. Acad. Sci. U.S.A.*, vol. 82, pp. 8057–8061, Dec. 1985, Plow et al.

*Primary Examiner*—Howard E. Schain
*Assistant Examiner*—Susan M. Perkins
*Attorney, Agent, or Firm*—Wegner, Cantor, Mueller & Player

[57] ABSTRACT

The subject of the invention is peptide derivatives corresponding to formula $$X^1 - X^2 - Gly - Asp - X^3 - X^4 \qquad (I)$$

in which:
- $X^1$ represents a hydrogen atom, a N-protecting group, an amino acid residue or a N-protected amino acid residue,
- $X^2$ represents a residue of L-Arg or D-Arg, L-Orn or D-Orn, N-aminocarbonyl-L-Orn or N-aminocarbonyl-D-Orn, or L-Lys, or D-Lys,
- $X^3$ represents a residue of L-Trp, D-Trp, L-Leu, D-Leu, L-Ile, D-Ile, L-Phe, D-Phe or a chain of 2 or 3 of these residues, and
- $X^4$ represents a -OH group, -NH$_2$ group, -OR$^1$ group in which R$^1$ represents an alkyl radical of C$_1$ to C$_4$, a NHR$^2$ group in which R$^2$ represents an alkyl radical of C$_1$ to C$_4$, or an amino acid residue.

These derivatives are useful in therapy on account of their platelet aggregation inhibiting activity.

5 Claims, No Drawings

NOVEL PEPTIDES HAVING PLATELER AGGREGATION INHIBITORY ACTIVITY

This application is a continuation of U.S. application Ser. No. 07/130,863 filed Dec. 10, 1987, now abandoned.

The present invention relates to new peptide derivatives possessing a platelet aggregation inhibiting activity, a process for their preparation and their uses in therapy and as diagnostic agents.

More precisely, the invention relates to peptide analogues of a sequence of fibrinogen which can be used in particular to antagonize the interaction between fibrinogen and blood platelets.

It is known that during the course of hemostatis blood platelets adhere to the sub-endothelium of the damaged vessel, secrete their granular contents after stimulation and aggregate together to form a platelet thrombus The aggregation depends on contacts which are established between membranes of adjacent platelets. This reaction is necessary for the cessation of bleeding. However, it exhibits numerous pathological deviations, in particular in cases of veinous or arterial thromboses, during the development of an atheroma plaque, or the formation of microthrombi which may obstruct the peripheral or cerebral microcirculation. The control and regulation of platelet aggregation are thus a major objective in the prevention of thrombosis and of atherosclerosis and numerous studies have been devoted to the research and development of molecules with platelet aggregation inhibiting properties.

Fibrinogen exercises an important role in this phenomenon. Thus, in the plasma of patients suffering from congenital afibrinogenemia, platelet aggregation is seriously reduced or absent and this deficiency is corrected by the injection of fibrinogen. Similarly, in the absence of fibrinogen washed platelets do not aggregate in the presence of ADP or epinephrine. The presence of fibrinogen is thus a necessity for the normal development of a platelet thrombus. The involvement of fibrinogen in aggregation is due to the induction of a specific receptor for this protein on the membrane of the activated platelet. All of the physiological stimuli of the platelet induce a unique class of receptor and the interaction of fibrinogen with this receptor regulates platelet aggregation. Thus, there exists a mechanism of platelet aggregation, common to all inducers, which depends on the interaction between fibrinogen and its receptor. The physiological importance of this path of platelet aggregation dependent on fibrinogen is attested to by the study of cases of Glanzmann thrombasthenia in which the platelets do not bind fibrinogen and do not aggregate in response to all of the physiological stimuli of the cell.

In summary, the fibrinogen receptor is not expressed by the circulating platelet, it is induced as soon as the cell is stimulated. This induction may be dependent on, or independent of, the secretion reaction. All of the stimuli induce the expression of the same receptor and the interaction between fibrinogen and the receptor lead directly to aggregation. The dissociation of the fibrinogen bound to the platelet results in the disaggregation of the platelets.

In this context, it is clear that if the interaction between fibrinogen and its platelet receptor could be regulated, this would constitute a means of controlling the aggregation in vitro and in vivo.

The aim of the present invention is precisely to provide new agents which make it possible to inhibit, regulate or measure selectively the pathway of aggregation dependent on fibrinogen.

Peptide sequences derived from the fibrinogen molecule have already been identified as inhibitors of the binding of this protein to platelets and thus as blockers of their aggregation. Thus, E. Plow et al. (Proc. Natl. Acad. Sci. USA 82 8057, 1985) have described the activity of the sequence Arg-Gly-Asp-Ser (RGDS) present in the alpha chain of fibrinogen.

*The meanings of the symbols and abbreviations used are given in the Appendix.

The subject of the present invention is peptide analogues of the C-terminus of the alpha chain of fibrinogen which exhibit an inhibitory effect on the fibrinogen-platelet interaction and on platelet aggregation.

These peptide derivatives correspond to the following general formula:

$$X^1\text{-}X^2\text{-Gly-Asp-}X^3\text{-}X^4 \qquad (I)$$

in which:
- $X^1$ represents a hydrogen atom, a N-protecting group, an amino acid residue or a residue of a N-protected amino acid,
- $X^2$ represents a residue of L-Arg or D-Arg, L-Orn or D-Orn, N-aminocarbonyl-L-Orn or N-aminocarbonyl-D-Orn, or L-Lys or D-Lys,
- $X^3$ represents a residue of L-Trp, D-Trp, L-Leu, D-Leu, L-Ile, D-Ile, L-Phe, D-Phe, D-Phe or a chain containing 2 or 3 of these residues, and
- $X^4$ represents a -OH group, $-NH_2$, $-OR^1$ group in which $R^1$ represents a $C_{1-4}$ alkyl radical, a $NHR^2$ group in which $R^2$ represents a $C_{1-4}$ alkyl radical, or an amino acid residue.

In the groups $X^1$ and $X^4$ the amino acid residues likely to be used are in particular those of L or D-pyroglutamyl, L or D-alanyl, glycyl, L or D-prolyl, L or D-valyl, L or D-phenylalanyl, L or D-homocysteinyl, L or D-aspartyl, L or D-glutamyl, L or D-histidyl, L or D-methionyl, L or D-threonyl, L or D-seryl, L or D-cysteinyl, L or D-leucyl, L or D-arginyl, L or D-tryptophanyl, L or D-tyrosyl, L or D-lysyl and L or D-ornithyl.

In the case in which $X^1 = X^4 = $Cys the peptide derivative can be cyclized through the formation of a disulfide bridge to give the compound of formula:

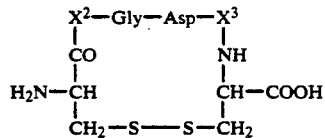

The physiologically acceptable N-protecting groups are in particular the groups which protect against attack at the N-terminal by exopeptidases. As examples of such groups mention may be made of the acyl groups such as t-butoxycarbonyl (Boc), t-amyloxycarbonyl (t-Aoc), benzyloxycarbonyl, benzoyl, acetyl, formyl, propanoyl, butanoyl, phenylacetyl, phenylpropanoyl, cyclo-pentylcarbonyl.

The present invention also includes the equivalents of the peptide derivatives of Formula I in which each peptide bond (—CO—NH—) between two amino acid residues of the general Formula I is replaced by the following structures:

CO—N(CH$_3$)—; —CO—O—; —CH$_2$—NH—; —CS—NH—;
CO—CH$_2$; CH$_2$—S—; —CHOH—CH$_2$—; —HN—CO—;
CH=CH—; —CH$_2$—CH$_2$—.
or in which one or more groups such as the groups —CH$_2$—, —NH—, —O— are intercalated into the peptide skeleton.

Preferred peptide derivatives are peptides of the formula:

H-Arg-Gly-Asp-Trp-OH and

H-Arg-Gly-Asp-Phe-OH

The present invention also has as its subject:
a pharmaceutical composition containing as its active principle a peptide derivative corresponding to Formula I
a diagnostic agent containing a peptide derivative corresponding to Formula I.

The peptide derivatives corresponding to Formula I can be prepared in a standard manner by means of liquid or solid phase peptide synthesis by successive couplings of the different amino acid residues to be incorporated (from the N-terminus to the C-terminus in liquid phase synthesis or from the C-terminus towards the N-terminus in solid phase synthesis) and the N-termini and the reactive side chain groupings of which are blocked prior to condensation by groups such as those mentioned below:

| 1) N-terminus protected by: | Boc Bpoc Fmoc |
|---|---|
| 2) Residue | Side chain protecting group |
| Alanyl | H |
| Arginyl | tosyl |
| Asparagyl | H,xanthyl |
| Aspartyl | O-benzyl |
| Cyst | acetamidomethyl (Acm), 4-methylbenzyl (Meb), 4-methoxybenzyl (Mob), S-benzyl |
| Glutamyl | O-benzyl |
| Glutaminyl | xanthyl |
| Glycyl | H |
| Hist dyl | tosyle, 2-4-dinitroohenyl (Dnp) |
| Isoleucyl | H |
| Leucyl | H |
| Lysyl | 2-chlorobenzyloxycarbonyl (Clz), trifluoroacetyl (TFA), formyl (For), benzyloxycarbonyl (Z) |

-continued

| Methionyl | H |
|---|---|
| Norleucyl | H |
| Ornithyl | benzyloxycarbonyl |
| Phenylalanyl | H |
| Propyl | H |
| Pyroglutamyl | H |
| Sarcosyl | H |
| Seryl | O-benzyl |
| Threonyl | H, O-benzyl |
| Tryptophanyl | H, formyl |
| Tyrosyl | H, 2-6-dichlorobenzyl (dcb), 2-bromo-benzyloxycarbonyl |
| Valyl | H |

Different types of coupling methods can be used:
1. Coupling of the residues with a carbodiimide (ex: DCC, EDC) with or without a catalyst (ex: HOBT) or any other coupling agent (ex: EEDQ).
2. Utilization of the amino acids in the form of preformed symmetrical anhydrides.
3. Utilization of the amino acids in the form of active esters (ex: p-nitrophenyl ester, HOBT ester) and coupling by the intermediary of DCC.

In solid phase peptide synthesis (SPPS) Table I below indicates the different types of resin which can be used as well as the appropriate protecting groups and methods for the different steps.

TABLE I

| SPPS system used | Pepside-resin linkage | Alpha N protection | Reagent for deprotection | Side chain protection | Cleavage reagent |
|---|---|---|---|---|---|
| standard | Benzyl ester | Boc | TFA, HCl | Benzyl | HF, HBr |
| Stable (long chain) | Pam | Boc | TFA, HCl | Benzyl | HF, HBr |
| | Benzyl ester | Bpoc | TFA (dilute) | Benzyl | HF |
| | Benzyl ester | Bpoc | TFA (dilute) | t-Butyl | HF |
| Labile | Ether resin | Bpoc | TFA (dilute) | t-Butyl | TFA |
| Orthogonal | Ether resin | Fmoc | Piperidine | t-Butyl | TFA |
| Synthesis of Fragments | Ether resin | Fmoc | Piperidine | Benzyl | TFA |
| | t-Butyl resin | Fmoc | Piperidine | Benyzl | TFA |
| | Hydrazide resin | Fmoc | Piperidine | Benzyl | TFA |
| Fragment condensation | Benzyl ester | Fmoc | Piperidine | Benzyl | HF |
| Peptides amides | MBHA, BHA | Boc | TFA, HCl | Benzyl | HF |
| Peptides alcohols | Benzyl ester | Boc | TFA, HCl | Benzyl | LiBH$_4$ |

In solid phase synthesis the first amino acid (C-terminal amino acid) to be attached to the resin can either be bought commercially already bound to the support or coupled to it by the intermediary of its cesium salt (Gisin's method), its tetramethylammonium salt (Loffet's method) or by a carbodiimide.

The following examples illustrate the preparation of the peptide derivatives corresponding to Formula I.

EXAMPLE 1

Synthesis of the peptide H-Arg-Gly-Asp-Trp-OH (or R G D W)

This peptide was synthesized on a solid phase starting from a presubstituted resin of the PAM type (4-(oxymethyl)-phenylacetamidomethyl), Boc-Trp(CHO)-PAM-resin, which is substituted with 0.34 mmol Trp/g. The protected amino acids used and the solvents in which they were dissolved were the following:

| Derivatives | Solvents |
|---|---|
| Boc-Asp (O Bzl) | DCM |
| Boc-Gly | DCM |

| Derivatives | Solvents |
| --- | --- |
| Boc-Arg (Tos) | DMF |

Each coupling was carried out using dicyclohexylcarbodiimide (DCC) catalyzed by hydroxybenzotriazole (HOBT), the reaction being allowed to proceed for 2 hours, and was followed by acetylation using acetic anhydride for 30 minutes.

During the synthesis, the deprotections were performed using trifluoroacetic acid (TFA) and the completeness of coupling was checked by the Kaiser test.

The final cleavage was carried out using HF (10 ml HF/g) in the presence of ethanedithiol (1 ml/10 ml HF) for 1 hour at 0° C. in order to cleave the tryptophan residue. After being washed with ether, the peptide was extracted by means of 45% acetic acid, then 10% acetic acid and lyophilized.

However, the formyl group (—CHO) used to protect the Trp during synthesis is resistant to hydrogen fluoride (HF). In order to cleave it a second treatment of the peptide is necessary:

For this purpose, the peptide RGDW (For) is treated for several hours with 75 ml of 0.03M hydroxylamine ($H_2N$—OH.HCl) adjusted to pH 9 by ammonia solution, the disappearance of the absorption due to the formyl group at 300 nm and the appearance of free tryptophan absorbing at 280 nm being monitored spectrometrically.

After being filtered through a Millex SR-0.5 u, the peptide obtained was purified on a column of Sephadex G 10 using 25% acetic acid as eluant, then it was lyophilized twice.

The amino acid analysis and the absorption spectrum of RGDW as well as thin layer chromatography and HPLC reveal a pure peptide product, free of other organic material but contaminated with a large amount of salt. This is explained by the prior deprotection treatment of tryptophan with $H_2N$—OH.HCl in the presence of $NH_4OH$ which leads to the formation of ammonium chloride which cannot be lyophilized. It is therefore necessary to remove the chlorides by anion exchange on a column of $AGl-X_2$ (acetate form) and the peptide is eluted by 0.1% acetic acid (pH 3.5). The ammonium acetate obtained can be lyophilized.

Control of Purity

1. Thin layer chromatography on silica with detection by:
   ninhydrin ($NH_2$)
   TDM (NH)
   Ehrlich reagent (paradimethylaminobenzaldehyde) (specific for Trp).

| Migration solvents | Rf. |
| --- | --- |
| Butanol-1/Acetic acid/Water 4 1 1 | 0.1 |
| Methanol/chloroform/25% ammonia 60 40 20 | 0.42 |

2. HPLC on an analytical column of Spherisorb OD5.2 5 u Eluant: gradient of acetonitrile (0.1% TFA) in water (0.1% TFA) from 0 to 80% in 25 mn at a flow rate of 1 ml/mn.

Detection: Optical density at 205-215 nm (peptide bond) and at 270-290 nm (Trp).

Retention T RGDW: 15 mn, i.e. at 48% acetonitrile (0.1% TFA).

3. Amino acid analysis

After hydrolysis at 110° C. for 27 hours by means of HCl/propionic acid (50/50) in the presence of mercaptoethanol (0.1%).

| | Molar equivalents |
| --- | --- |
| Trp | ND |
| Asp | 1 |
| Gly | 0.92 |
| Arg | 0.95 |

EXAMPLE 2

Synthesis of the peptide H-Arg-Gly-Asp-Phe-OH (or R G D F)

This peptide was synthesized on a solid phase using the following procedures:
   support: chloromethylated Merrifield resin (0.7 mmol Cl/g) containing 2% of divinylbenzene.

Preparation of Boc-Phe-resin

To 7.5 mmoles (2 g) of Boc-Phe-OH dissolved in 10 ml of ethanol are added 3.75 mmoles (1.22 g) of $Cs_2CO_3$ in 2 ml of water. The cesium salt formed (Boc-Phe-OCs, 7.5 mmol) after several minutes of stirring was evaporated to dryness and stored in a vacuum in a dessicator for 48 h. It was then redissolved in 80 ml of DMF and mixed with 10.7 g of resin (0.7 mmol Cl). The reaction was carried out with stirring in a bath heated to 50° C. for 24 h. The derivatized resin (Boc-Phe-resin) was then filtered off and washed with DMF, $DMF/H_2O$, DMF, EtOH, then dried in a vacuum for 3 h. The degree of substitution of the resin was calculated by amino acid analysis after hydrolysis at 150° C. for 3 h. by means of the HCl/propionic acid (50/50) mixture. The degree of substitution obtained was about 0.24 mmol Phe/g resin.
   coupling:

All of the amino acid derivatives incorporated were coupled by the carbodiimide DCC method in the presence of the catalyst HOBT (2 equivalents of amino acid, DCC and HOBT with respect to the Phe).

The protected amino acid derivatives used and the solvent in which they were dissolved were the following:

| Derivatives | Solvents |
| --- | --- |
| Boc-Asp-O-Bzl | DCM |
| Boc-Gly | DCM |
| Boc-Arg (Tos) | DMF |

The couplings were allowed to proceed in DCM for 2 h.

The deprotections by means of TFA and the completeness of coupling were all checked by the Kaiser test.
   cleavage:

The cleavage of the synthesized peptide was carried out using HF (10 ml/g resin) in the presence of anisole (1 ml/g resin) for 1 h. at 0° C. After being washed with ether, the peptide was then extracted with 15% acetic acid and lyophilized.
   purification: on a column of Sephadex G10 using 10% acetic acid as eluant.
   control:

amino acid analysis: after hydrolysis in HCl/propionic acid (50/50) for 30 mn at 150° C.
thin layer chromatography on silica:
eluant: CH$_3$OH/CHCl$_3$/25% NH$_4$OH (60/40/20)
detection: phenanthroquinone (Arg), ninhydrin (NH$_2$), TDM (NH)
R$_f$=0.51
eluant 2: 2-butanone/CH$_3$COOH/H$_2$O (10/30/25)
R$_f$=0.73
eluant 3: butanol/CH$_3$COOH/H$_2$O (75/10/24)
R$_f$=0.16.

EXAMPLE 3

Synthesis of the peptide H-Leu-Arg-Gly-Asp-Phe-OH (or L R G D F).

This peptide was synthesized, purified and analyzed using the same methods as those described for the peptide synthesized in Example 1.

Its analytical properties are as follows:
thin layer chromatography on silica:
eluant 1: CH$_3$OH/CHCl$_3$/25% NH$_4$OH (60/40/20).
R$_f$=0.82
eluant 2: 2-butanone/CH$_3$COOH/H$_2$O (10/30/25)
R$_f$=0.69
eluant 3: butanol/CH$_3$COOH/H$_2$O (75/10/24)
R$_f$=0.21

Given below are the results of the pharmacological studies which demonstrate the properties of the peptide derivatives corresponding to Formula I 1. Inhibition of platelet-fibrinogen binding Preparation of the platelets

| ACD has the following composition: | |
|---|---|
| Citric acid | 3.41 g |
| Trisodium citrate 5H$_2$O | 5.95 g |
| Dextrose | 5 g |
| H$_2$O make up to | 250 ml |

The blood is then centrifuged for 20 mn at a 1,000 r/mn (JOUAN E 96 centrifuge) at room temperature.

The PRP (plasma rich in platelets) is decanted and treated with 0.1 µM PGE$_1$, then centrifuged for 15 mn at 2,000 r/mn.

The platelets obtained in the pellet are then taken up in 1 ml of Tyrode buffer-albumin, pH 7.2, prepared with the following composition:

| Tyrode Buffer (stock solution) | |
|---|---|
| NaCl | 1.3 M |
| KCl | 0.026 M |
| NaHCO$_3$ | 0.12 M |
| Tyrode buffer-albumin: | |

| -continued | |
|---|---|
| Stock solution | 1/10 M |
| D-glucose | 0.0055 M |
| albumin | 2% |
| 1 M HCl to give pH | 7.2 |

The platelets are washed on a column of Sepharose CL 2B using Tyrode buffer-albumin, pH 7.2, then the platelets are recovered and diluted to a concentration of 2×10$^8$ platelets/ml.

The assays are carried out on 4×10$^7$ platelets in the presence of CaCl$_2$ (0.5 mM), $^{125}$I-fibrinogen 0.1×10$^{-6}$M) and different concentrations of peptide, and the stimulation of the platelets is induced by ADP (5×10$^{-6}$M). After incubation for 15 mn and deposition on a 15% saccharose solution the $^{125}$I-fibrinogen-platelet complex is isolated by centrifugation at 12,000 r/mn for 2 mn.

The results are presented in Table II in the form of CI50. This table also presents the sequence of the peptides.

2. Inhibition of platelet aggregation

The effect of the synthetic peptides on platelet aggregation was studied on platelets isolated as previously described for the study of the binding to fibrinogen. The stimulation of the platelets was also brought about by 5×10$^{-6}$M ADP and the assay was carried out in the presence of 1.1×10$^{-6}$M fibrinogen and of 0.5×10$^{-6}$M CaCl$_2$.

The results are presented in Table II and demonstrate an inhibitory activity of the peptides corresponding to Formula I on platelet aggregation.

TABLE II

| Peptide | Nomenclature | Inhibition IC50 (µM) | |
|---|---|---|---|
| | | Platelet-fibrinogen binding | Aggregation |
| Arg-Gly-Asp-Trp | RGDW | 3.6 | 10 |
| Arg-Gly-Asp-Phe | RGDF | 7 | 15 |
| Leu-Arg-Gly-Asp-Phe | LRGDF | 20 | 20 |

The peptide derivatives corresponding to Formula I can be used in particular for the treatment and prevention of thromboses, in particular in prethrombotic states in order to block platelet aggregation.

They are also able to exert an inhibitory effect on:
the adhesion of blood platelets to endothelial cells of the vascular walls or of the sub-endothelium.
atherogenesis
the development of metastases
the inflammatory response.

The therapeutic compositions according to the invention may be administered to man and to animals by the oral or the parenteral route.

They can exist in the form of solid, semi-solid or liquid preparations. As examples may be cited tablets, gelatine capsules, injectable solutions or suspensions.

In these compositions the active principle is usually mixed with one or more of the usual, pharmaceutically acceptable excipients well-known to the specialist.

The therapeutic composition may contain in particular from 1 to 60% by weight of the active principle.

The amount of active principle administered obviously depends on the patient who is being treated, the route of administration and the severity of the disease. It usually varies from 1 to 5,000 mg.

| Abbreviations commonly used in peptide chemistry | |
|---|---|
| BHA: | benzylnydrylamine (resin) |
| Boc: | |
| Bpoc: | 2-(4-biohenylyl)propyl(-2)oxycarbonyl |
| Bzl: | benzyl |
| Clz: | 2-chlorobenzyloxycarbonyl |
| DCC: | dicyclohexylcarbodiimid |
| DCM: | dichloromethane |
| DMF: | dimethylformamide |
| EDC: | N-ethyl-N'-(3-dimethylaminopropyl) carbodiimide |
| EEDQ: | N-ethyloxycarbonyl-2-ethyloxy-1,2-dihydroquinoline |
| Fmoc: | 9-fluorenylmethyloxycarbonyl |
| HOBT: | 1-hydroxybenzotriazole |
| MBHA: | 4-methylbenzhydrylamine (resin) |
| TDM: | N,N,N',N',tetramethyl-4,4'-diaminodiphenylmethane |
| TFA: | |
| Tos: | tosyl |
| Xan: | xanthyl |
| Symbols for the amino acids | | |
|---|---|---|
| A | Ala | alanine |
| C | Cys | cysteine |
| D | Asp | aspartic acid |
| E | Glu | glutamlic acid |
| F | Phe | phenylalanine |
| G | Gly | glycine |
| H | His | histidine |
| I | Ile | isoleucine |
| K | Lys | lysine |
| L | Leu | leucine |
| M | Met | methionine |
| N | Asn | asparagine |
| P | Pro | proline |
| Q | Gln | glutamine |
| R | Arg | arginine |
| S | Ser | serine |
| T | Thr | threonine |
| V | Val | valine |
| W | Trp | tryptophane |
| Y | Tyr | tyrosine |

What I claim is:

1. A compound selected from the compounds of the general formula $X^1$-$X^2$-Gly-Asp-$X^3$-$X^4$ (I)

in which:

$X^1$ is selected from the group consisting of hydrogen and a N-protecting group, $X^2$ is selected from a residue of L-Arg, D-Arg, L-Orn, D-Orn, N-aminocarbonyl -L-Orn, N-aminocarbonyl-D-Orn, L-Lys and D-Lys, $X^3$ is selected from a residue of L-Trp, D-Trp, L-Leu, D-Leu, L-Ile, and D-Ile, and $X^4$ is selected from the group consisting of —OH, —$NH_2$, —$OR^1$ in which $R^1$ is $C_{1-4}$ alkyl, and $NHR^2$ in which $R^2$ is $C_{1-4}$ alkyl.

2. Peptide of the formula

H-Arg-Gly-Asp-Trp-OH.

3. A therapeutic composition for the treatment and the prevention of thromboses comprising an effective amount of a compound as claimed in claim 1 in admixture with a pharmaceutically acceptable excipient.

4. A composition as claimed in claim 3, in which the compound is

H-Arg-Gly-Asp-Trp-OH.

5. A process for the treatment and the prevention of thromboses, which comprises administering to a human in need thereof an effective amount of a compound selected from the compounds of the general formula $X^1$-$X^2$-Gly-Asp-$X^3$-$X^4$ (I)

in which:

$X^1$ is selected from the group consisting of hydrogen and a N-protecting group, $X^2$ is selected from a residue of L-Arg, D-Arg, L-Orn, D-Orn, N-aminocarbonyl -L-Orn, N-aminocarbonyl-D-Orn, L-Lys and D-Lys, $X^3$ is selected from a residue of L-Trp, D-Trp, L-Leu, D-Leu, L-Ile, and D-Ile, and $X^4$ is selected from the group consisting of —OH, —$NH_2$, —$OR^1$ in which $R^1$ is $C_{1-4}$ alkyl, and $NHR^2$ in which $R^2$ is $C_{1-4}$ alkyl.

* * * * *

UNITED STATES PATENT AND TRADEMARK OFFICE
CERTIFICATE OF CORRECTION

PATENT NO. : 5,100,875
DATED : March 31, 1992
INVENTOR(S) : Gerard A. MARGUERIE de ROTROU It is certified that error appears in the above-identified patent and that said Letters Patent is hereby corrected as shown below:

On the Title page,

Please correct the title to read:

Item [54] NOVEL PEPTIDE HAVING PLATELET AGGREGATION INHIBITORY ACTIVITY THERAPY--

Signed and Sealed this

Seventeenth Day of August, 1993

Attest:

BRUCE LEHMAN

Attesting Officer

Commissioner of Patents and Trademarks